(12) United States Patent
Sterling

(10) Patent No.: US 7,662,122 B2
(45) Date of Patent: Feb. 16, 2010

(54) ORTHOTIC OR PROSTHETIC DEVICES WITH ADJUSTABLE FORCE DOSIMETER AND SENSOR

(75) Inventor: Shane Sterling, Seattle, WA (US)

(73) Assignee: Bellacure, Inc., Seattle, WA (US)

( * ) Notice: Subject to any disclaimer, the term of this patent is extended or adjusted under 35 U.S.C. 154(b) by 415 days.

(21) Appl. No.: 11/074,949

(22) Filed: Mar. 7, 2005

(65) Prior Publication Data

US 2006/0200057 A1 Sep. 7, 2006

(51) Int. Cl.
- *A61F 5/00* (2006.01)
- *A61F 13/00* (2006.01)
- *A61F 13/06* (2006.01)

(52) U.S. Cl. .............. 602/26; 602/5; 602/16; 602/23; 602/60; 602/61; 602/62; 128/882

(58) Field of Classification Search .......... 602/16, 602/20, 23, 26–27; 484/124; 128/882
See application file for complete search history.

(56) References Cited

U.S. PATENT DOCUMENTS

| | | |
|---|---|---|
| 667,768 A | 2/1901 | Puy |
| 1,227,700 A | 5/1917 | Tucker |
| 1,510,408 A | 9/1924 | Lychou |
| 2,195,024 A * | 3/1940 | Bullock .............. 602/26 |
| 2,467,907 A | 4/1949 | Peckham |
| 3,046,981 A | 7/1962 | Biggs, Jr. et al. |
| 3,528,412 A | 9/1970 | McDavid et al. ........ 128/80 |
| 3,581,741 A | 6/1971 | Rosman et al. ........ 128/80 |
| 3,736,436 A | 5/1973 | Crites .................. 307/88 |
| 3,945,046 A | 3/1976 | Stromgren .............. 2/22 |
| 4,067,070 A * | 1/1978 | Seamone et al. ....... 623/24 |
| 4,240,414 A | 12/1980 | Theisler .............. 128/80 |
| 4,269,181 A | 5/1981 | Delannoy ............ 128/156 |

(Continued)

FOREIGN PATENT DOCUMENTS

EP 0 050 769 5/1982

(Continued)

OTHER PUBLICATIONS

Innovation Sports XCL System Brochure, pp. 1-2.

(Continued)

*Primary Examiner*—Patricia M Bianco
*Assistant Examiner*—Brandon Jackson
(74) *Attorney, Agent, or Firm*—Dorsey & Whitney LLP

(57) ABSTRACT

An orthotic knee brace for treating unicompartmental osteoarthritis in a knee joint is described. The brace includes a fabric sleeve mounting and a bracing member removably positioned in the sleeve to provide a therapeutic force on the joint. The force is applied by a force dosimeter assembly that draws an incrementally adjustable amount of force on cables connected to the bracing member. The amount of force applied by the force dosimeter is detected by a force sensor, and is indicated by a force indicator, each also removably attachable on the fabric sleeve mounting. The foregoing features, while exemplified in the context of a knee brace, are adaptable to any orthotic or prosthetic device where it is desired to apply an adjustable amount of force to a point on the device to provide a therapeutic benefit, and to provide a real-time indication to the user of the amount of force being applied.

18 Claims, 11 Drawing Sheets

U.S. PATENT DOCUMENTS

| | | | |
|---|---|---|---|
| 4,275,716 A | 6/1981 | Scott, Jr. | 128/80 |
| 4,296,744 A | 10/1981 | Palumbo | 128/80 |
| 4,381,768 A | 5/1983 | Erichsen et al. | 128/80 |
| 4,506,661 A | 3/1985 | Foster | 128/80 |
| 4,528,440 A | 7/1985 | Ishihara | 219/370 |
| 4,554,913 A | 11/1985 | Womack et al. | 128/80 |
| 4,572,170 A | 2/1986 | Cronk et al. | 128/80 |
| 4,632,098 A | 12/1986 | Grundei et al. | 128/80 |
| 4,688,559 A | 8/1987 | Vito et al. | 128/80 |
| D292,529 S | 10/1987 | Saare | D24/64 |
| D298,568 S | 11/1988 | Womack et al. | D24/64 |
| 4,796,610 A | 1/1989 | Cromartie | 128/80 |
| 4,805,606 A | 2/1989 | McDavid, III | 128/80 |
| 4,854,308 A | 8/1989 | Drillio | 128/80 |
| 5,016,621 A | 5/1991 | Bender | 128/80 |
| 5,085,210 A | 2/1992 | Smith, III | 602/26 |
| 5,267,951 A | 12/1993 | Ishii | 602/26 |
| 5,277,697 A | 1/1994 | France et al. | 602/16 |
| 5,277,698 A | 1/1994 | Taylor | 602/26 |
| 5,288,287 A | 2/1994 | Castillo et al. | 602/16 |
| 5,302,169 A | 4/1994 | Taylor | 602/16 |
| 5,344,135 A | 9/1994 | Isobe et al. | 271/180 |
| 5,383,845 A | 1/1995 | Nebolon | 602/26 |
| 5,409,449 A | 4/1995 | Nebolon | 602/16 |
| 5,415,625 A | 5/1995 | Cassford et al. | 602/26 |
| 5,431,623 A | 7/1995 | Rice | 602/26 |
| 5,445,602 A | 8/1995 | Grim et al. | 602/27 |
| 5,449,341 A | 9/1995 | Harris | 602/63 |
| 5,458,565 A | 10/1995 | Tillinghast, III et al. | 602/26 |
| 5,460,599 A | 10/1995 | Davis et al. | 602/26 |
| 5,464,383 A | 11/1995 | Padden et al. | 602/20 |
| 5,474,524 A | 12/1995 | Carey | 602/26 |
| 5,512,039 A | 4/1996 | White | 602/26 |
| D372,983 S | 8/1996 | Nebolon | D24/190 |
| 5,542,911 A | 8/1996 | Cassford et al. | 602/26 |
| 5,562,605 A | 10/1996 | Taylor | 602/26 |
| 5,695,452 A | 12/1997 | Grim et al. | 602/6 |
| 5,766,140 A | 6/1998 | Tillinghast, III et al. | 602/16 |
| 5,823,981 A | 10/1998 | Grim et al. | 602/26 |
| 5,857,988 A | 1/1999 | Shirley | 602/26 |
| 5,857,989 A | 1/1999 | Smith, III | 602/26 |
| 5,865,776 A | 2/1999 | Springs | 602/26 |
| 5,873,848 A | 2/1999 | Fulkerson | 602/62 |
| 5,934,599 A | 8/1999 | Hammerslag | 242/396 |
| 6,010,474 A | 1/2000 | Wycoki | 602/23 |
| 6,063,048 A | 5/2000 | Bodenschatz et al. | 602/62 |
| 6,110,138 A | 8/2000 | Shirley | 602/26 |
| 6,142,965 A | 11/2000 | Mathewson | 602/62 |
| 6,202,953 B1 | 3/2001 | Hammerslag | 242/396.1 |
| 6,245,034 B1 | 6/2001 | Bennett et al. | 602/20 |
| 6,250,651 B1 | 6/2001 | Reuss et al. | 280/14.21 |
| RE37,297 E | 7/2001 | Smith, III | 602/26 |
| 6,267,741 B1 | 7/2001 | Lerman | 602/18 |
| 6,287,268 B1 | 9/2001 | Gilmour | 602/26 |
| 6,287,269 B1 | 9/2001 | Osti et al. | 602/62 |
| 6,289,558 B1 | 9/2001 | Hammerslag | 24/68 |
| 6,327,918 B1 | 12/2001 | Lawless | 73/863.21 |
| 6,368,295 B1 | 4/2002 | Lerman | 602/17 |
| 6,461,318 B2 | 10/2002 | Freeman et al. | 602/23 |
| 6,540,703 B1 | 4/2003 | Lerman | 602/5 |
| 6,540,709 B1 | 4/2003 | Smits | 602/26 |
| D477,409 S | 7/2003 | Mills et al. | D24/190 |
| 6,592,538 B1 | 7/2003 | Hotchkiss et al. | 602/26 |
| 6,592,539 B1 | 7/2003 | Einarsson et al. | 602/62 |
| 6,666,894 B2 | 12/2003 | Perkins et al. | 623/36 |
| 6,890,314 B2 | 5/2005 | Seligman | 602/26 |
| 6,898,826 B2 | 5/2005 | Draper et al. | 24/68 SK |
| 6,969,364 B2 | 11/2005 | Sterling | 602/16 |
| 6,969,365 B2 | 11/2005 | Scorvo | 602/16 |
| 7,076,843 B2 * | 7/2006 | Sakabayashi | 24/68 SK |
| 2001/0020143 A1 | 9/2001 | Stark et al. | 602/13 |
| 2002/0077574 A1 | 6/2002 | Gildersleeve et al. | 602/16 |
| 2002/0082542 A1 | 6/2002 | Hall | 602/60 |
| 2002/0095750 A1* | 7/2002 | Hammerslag | 24/68 SK |
| 2003/0032907 A1 | 2/2003 | Prahl | 602/16 |
| 2003/0204156 A1 | 10/2003 | Nelson et al. | 602/26 |
| 2003/0204938 A1 | 11/2003 | Hammerslag | 24/68 |
| 2004/0054311 A1 | 3/2004 | Sterling | 602/26 |
| 2004/0176715 A1 | 9/2004 | Nelson | 602/26 |
| 2004/0199095 A1 | 10/2004 | Frangi | 602/26 |
| 2004/0225245 A1 | 11/2004 | Nelson | 602/26 |
| 2004/0267179 A1 | 12/2004 | Lerman | 602/26 |
| 2005/0038367 A1 | 2/2005 | McCormick et al. | 602/26 |
| 2005/0159691 A1 | 7/2005 | Turrini et al. | 602/16 |
| 2006/0135900 A1 | 6/2006 | Ingimundarson et al. | 602/26 |
| 2006/0135901 A1 | 6/2006 | Ingimundarson et al. | 602/26 |
| 2006/0135902 A1 | 6/2006 | Ingimundarson et al. | 602/26 |
| 2006/0135903 A1 | 6/2006 | Ingimundarson et al. | 602/26 |
| 2006/0135904 A1 | 6/2006 | Ingimundarson et al. | 602/26 |
| 2006/0156517 A1 | 7/2006 | Hammerslag et al. | 24/68 |
| 2008/0228119 A1 | 9/2008 | Ingimundarson et al. | 602/16 |

FOREIGN PATENT DOCUMENTS

| | | |
|---|---|---|
| FR | 2 399 811 | 3/1979 |
| FR | 2 553 996 | 5/1985 |
| GB | 2 136 294 A | 9/1984 |
| WO | 88/01855 | 3/1988 |
| WO | 94/00082 | 1/1994 |
| WO | 2006/069221 | 6/2006 |
| WO | 2006/069222 | 6/2006 |

OTHER PUBLICATIONS

Unloader One® Brochure, Össur.

Pollo, Fabian et al., "Reduction of Medial Compartment Loads with Valgus Bracing of the Osteoarthritic Knee," *American Journal of Sports Medicine* 30(3): pp. 414-421, Jun. 2002.

Pollo, Fabian et al., "Braces: Bracing for the Osteoarthritic Knee," *Biomechanics*, Jun. 1997 <http:www.biomech.com/db_area/archives/1997/9706braces.bio.html>.

Pollo, Fabian and Robert W. Jackson, "Knee Bracing for Unicompartmental Osteoarthritis," *Journal of the American Academy of Orthopaedic Surgeons* 14(1): pp. 5-11, Jan. 2006.

Pollo, Fabian, "Book Review of: Basic Orthopaedic Biomechanics Edited by Mow VC and Hayes WC," *Annals of Biomedical Engineering* 21: pp. 189-190, 1993.

"Flex Stable Knee Support #8153|Otto Bock," <http://www.ottobockus.com/products/shelf_ orthotics/lower_extremity_3019. asp> accessed Jun. 5, 2006.

"Lerman 3-*Point* Knee Orthosis: A clinical and cost effective orthotic solution," Becker Orthopedic, Rev. 0-3/03.

"Lerman 3-Point Knee Orthosis: Pre-fitting preparation," Becker Orthopedic, Mar. 18, 2003.

Cascade Information Sheet containing "R. Lerman 3-point Orthosis".

"Bauerfeind. Motion is life," Bauerfeind USA homepage, <http://www.bauerfeindusa.com/html gbaktuelles news.php4> accessed Apr. 17, 2006.

"Bellacure: Restore Your Lifestyle," <http://www.bellacure.com/> accessed Apr. 17, 2006.

"Products of dj Orthopedics, LLC," <http://www.djortho.com/products/featoadjuster.html> accessed Apr. 17, 2006.

"Knee braces for knee pain, swelling and after surgery at the Knee Shop," pp. 1-2, <http://www.kneeshop.com> accessed Apr. 17, 2006.

"Mueller Sports Medicine—Knee Braces, Sleeves & Supports," <http://www.muellersportsmed.com/kneeproducts.htm> accessed Apr. 17, 2006.

"FLA Orthopedics, Inc.—Orthopaedic by Design®," <http://www.flaorthopedics.com> accessed Apr. 17, 2006.

"Innovation Sports," <http://www.innovationsports.com> accessed Apr. 17, 2006.

"dj Orthopedics manufactures and distributes orthopedic rehabilitation and support product . . . " <http://www.djortho.com/> accessed Apr. 17, 2006.

"Products>Catalog," <http://www.seattlesystems,com/products/catalog app/index.cfm?catSelect=3&subCatSelec . . . > accessed Apr. 17. 2006.

Donjoy Opal™ Information Sheet.

062AQ Vishay Micro-measurements Document No. 11080, Revision: Mar. 31, 2005.

Bauerfeind SofTec® OA Information Sheet .

U.S. Appl. No. 60/637,754, filed Dec. 22, 2004, Ingimundarson et al.

U.S. Appl. No. 60/684,163, filed May 25, 2005, Ingimundarson et al.

U.S. Appl. No. 60/739,407, filed Nov. 25, 2005, Ingimundarson et al.

Complaint for Injunctive Relief and Damages, *Ossur Holdings, Inc. et al*. v. *Bellacure, Inc. et al*., No. CV05-1552 (W.A.W.D., filed Sep. 9, 2005).

Declaration of Shane Sterling, *Ossur Holdings, Inc. et al*. v. *Bellacure, Inc. et al*., No. CV05-1552 (W.A.W.D., filed Sep. 9, 2005).

Plaintiffs' Motion for Temporary Restraining Order and Order to Show Cause and for Order Preserving Evidence and Permitting Expedited Discovery, *Ossur Holdings, Inc. et al*. v. *Bellacure, Inc. et al*., No. CV05-1552 (W.A.W.D., filed Sep. 9, 2005).

Plaintiffs' Reply Memorandum in Support of Its Motion for Preliminary Injunction, *Ossur Holdings, Inc. et al*. v. *Bellacure, Inc. et al*., No. CV05-1552 (W.A.W.D., filed Sep. 9, 2005).

Jerosch, J. et al., "Secondary Effects of Knee Braces on the Intracompartmental Pressure in the Anterior Tibial Compartment," Acta Orthopaedica Belgica, vol. 61, No. 1, 1995, pp. 37-42.

Kelley, M., "Nonsurgical management of osteoarthritis of the knee," JAAPA, vol. 19, No. 1, Jan. 2006, pp. 26-32.

"Sports knee brace and medical knee braces for joint injuries," Push Braces of Holland, Push Care Knee Braces product information, available at http://www.pushstore.co.uk/listproducts-K0001/Knee_support_braces.html, as accessed on Jan. 21, 2009.

"Professional Orthopedic and Sports Physical Therapy: Treatment: Medial Collateral Ligament Injury,"http://www.professionalpt.com/index.php~practiceId=10018&lib=TreatmentPrint&dir=treatment&noheader=y&categoryId=195.html, as accessed on Jan. 21, 2009.

"Medial Collateral Ligament Injury," http://www.ourhealthnetwork.com/conditions/knee/MedialcollateralLigamentInjury.asp, as accessed on Jan. 21, 2009.

"The Use of the Knee Braces," American Academy of Orthopaedic Surgeons, Position Statement 1124, Oct. 1987, Revised Dec. 2003, 6 pages.

* cited by examiner

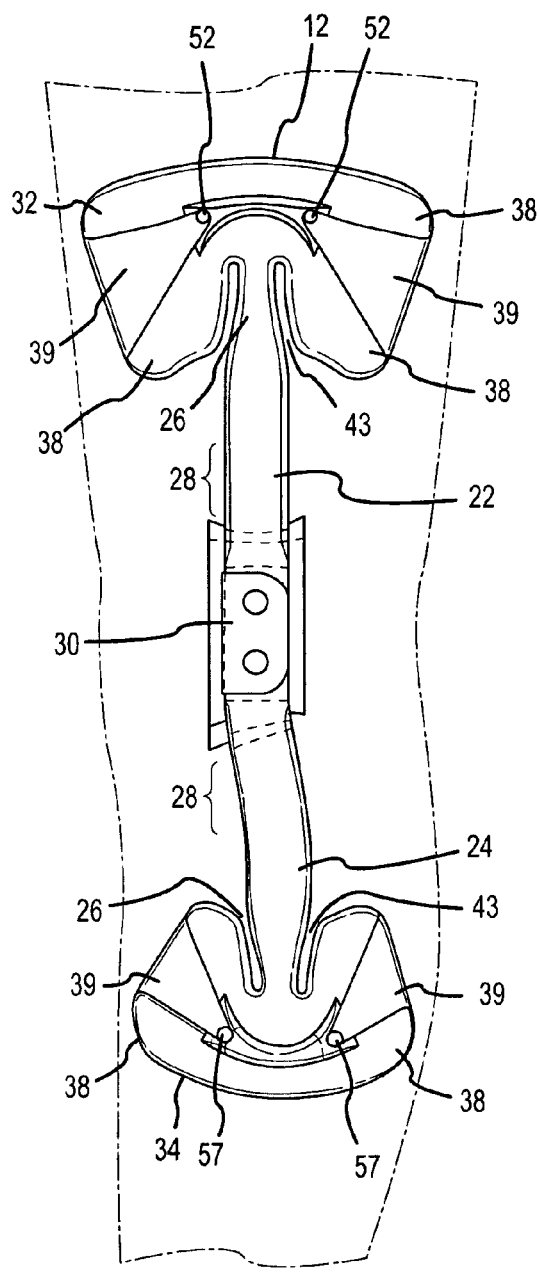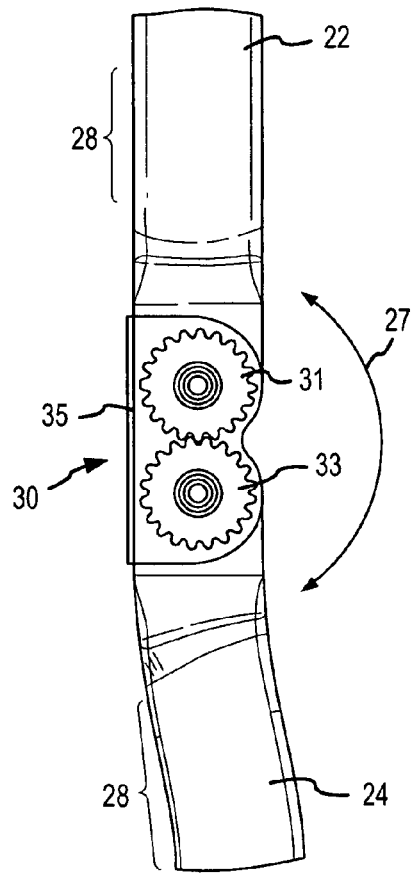
FIG. 3A
FIG. 3B

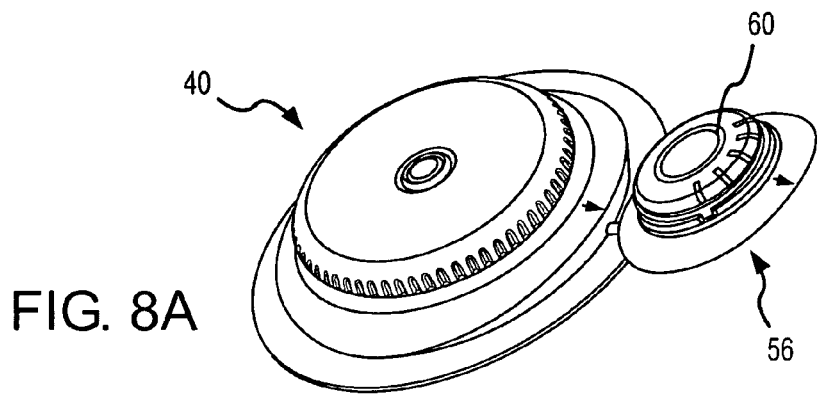
FIG. 8A
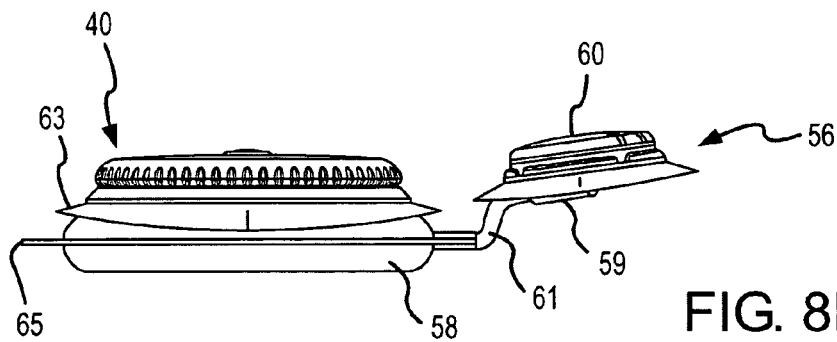
FIG. 8B
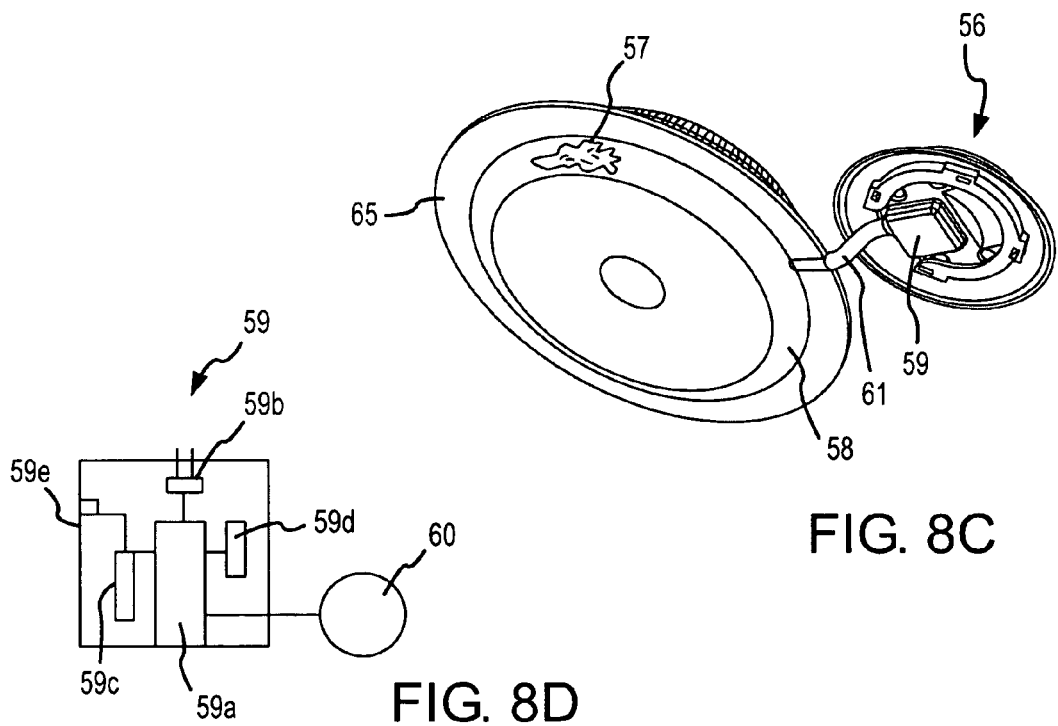
FIG. 8C
FIG. 8D

ORTHOTIC OR PROSTHETIC DEVICES WITH ADJUSTABLE FORCE DOSIMETER AND SENSOR

TECHNICAL FIELD

The application relates to orthotic and prosthetic devices generally, and in particular embodiments, to a knee brace, which include mechanisms for adjustably applying a force, sensing the amount of force applied and displaying an indication of the amount of applied force.

BACKGROUND

A variety of knee braces are known in the art for treating a variety of conditions of the knee. One condition is unicompartmental osteoarthritis, where one compartment side of the knee joint is deteriorated. To treat this condition with a knee brace requires a brace construction that is configured to urge the femur and tibia apart on the affected side of the knee.

One example brace system for treating unicompartmental osteoarthritis is described in U.S. Pat. No. 5,277,698. In this brace system, torsional strapping is used in conjunction with a rigid bracing member to provide forces to separate the affected compartment. One problem with this brace system is that it is difficult to reproducibly wrap the straps into the proper therapeutic position to reproducibly apply the same amount of force that is needed. U.S. Pat. No. 5,302,169 describes a rigid knee bracing member that could, if properly configured with appropriate strapping, be used to affect the therapeutic forces needed to treat unicompartmental osteoarthritis. That patent likewise does not describe any way to adjustably apply a different amount of force nor any method for reproducibly doing the same each time the brace is donned.

There remains a need in the art for orthotic devices generally, and for knee braces particularly, where the same amount of force can be easily and adjustably applied to affect a therapeutic benefit, and which can be reproducibly applied, detected and indicated, each time the brace is donned.

SUMMARY OF THE INVENTION

Described herein are devices for controlling forces applied by an orthotic or prosthetic device. In one aspect, the devices include a force dosimeter mounted to the orthotic or prosthetic device and operably connected to force a transmitting element to apply an adjustable amount of force to at least one point on the orthotic or prosthetic device. A force sensor mounted to the orthotic or prosthetic device is operably configured to detect the amount of force applied. An indicator mounted to the orthotic or prosthetic device is operably configured with the force sensor to indicate the amount of force applied.

In typical embodiments, the force sensor is configured with a transducer that converts the detected amount of force into an electrical signal. In certain embodiments, the transducer may be configured with a processor configured with instructions to control the indication provide by the indicator. The processor may be further configured with a memory and with instructions to store data pertaining to the amount of force applied at a given time when the orthotic or prosthetic device is in use by a subject. In certain embodiments, the processor is further configured with a data communication device for communicating data regarding the applied force in real time, or data stored in the memory to an external device. In certain examples, the data communication device uses a wireless protocol, such as a BlueTooth protocol.

In another aspect, there is described an orthotic device for treating a joint of a subject that includes a fabric sleeve conformed to fit on a limb of the subject. A pocket formed in the fabric sleeve is configured to removably hold a bracing member in at least one of a lateral or medial therapeutic position with respect to a joint on the limb when the orthotic device is worn by the subject. In an exemplary embodiment, the orthotic device is conformed to fit onto the subject's knee. In typical embodiments, the bracing member includes an upper bracing arm and a lower bracing arm. The upper and lower bracing arms are interconnected through a pivoting member that pivots about an axis parallel to or colinear with an axis of rotation of the joint. In certain embodiments, the pocket encloses the bracing member and is configured with a zipper to removably hold the bracing member.

In a different aspect there is described a bracing assembly, where at least one of the upper and lower bracing arms is configured to have a cross sectional dimension that is greater at a proximal end connected to the pivoting member than at a distal end extended away from the pivoting member. This provides less torsional and flexing resistance at the distal end than at the proximal end. The distal end of the upper bracing arm is joined to an upper shell contoured to fit the limb and the distal end of the lower bracing joins a lower shell contoured to fit the limb. In certain embodiments at least one of the upper and lower bracing arms have a thickness or a width that is greater at the proximal end than at a distal end. In certain embodiments, the distal end tapers from a greater dimension to the lesser dimension. In certain embodiments, at least one of the upper and lower shell members is configured with adjacent wing members extending in opposing directions away from a central joining region and the distal end is joined to its corresponding shell member at the central joining region.

In yet another aspect there is described an orthotic or prosthetic device, that includes a mounting conformed to fit the orthotic or prosthetic device on a limb of a subject and a bracing member engaged with the mounting to position the bracing member in a therapeutic position with respect to a joint on the limb of the subject when worn by the subject. The device includes a force dosing device and a tensioning device engaged with the mounting, and connected to the bracing member at a first end and connected to force transmitting element at a second end. The dosing device is operably connected to the tensioning device to adjust an amount of force applied to the bracing member through the force transmitting element. A force sensor is mounted between the tensioning device and the mounting to detect the amount of force applied. The device further includes an indicator mounted on the mounting and operably connected to the force sensor to display an indication of the amount of force applied.

In various embodiments, the force transmitting element can be selected from the group consisting of a cable, a strap and a net. In certain embodiments, the force transmitting element is a single cable. In other embodiments, the force transmitting element includes a plurality of cables attached to the bracing member at a plurality of positions on the bracing member. In certain of these embodiments, the force applied by the tensioning device is simultaneously applied to the plurality of cables when the force is adjusted with the dosimeter. In a particular embodiment, at least two of the plurality of cables attached to the bracing member at a plurality of positions form an "X" pattern on a lateral side of the device opposite the bracing member. The vertex of the X is positionable parallel to, or colinear with, an axis of rotation of the subjects joint.

In certain embodiments, the tensioning device comprises at least one torsion spring attached to the force transmitting element. In embodiments that use a plurality of cables as force transmitting elements, the tensioning device includes a plurality of torsion springs independently attached to the plurality of cables where each torsion spring is simultaneously adjustable by the force dosimeter.

In certain embodiments, the dosing device comprises a ratchet assembly that engages the tensioning device in a first position to incrementally increase the amount of force applied, and which engages the tensioning device in a second position to decrease the amount of force applied.

In various embodiments, the mounting for the brace apparatus is formed as a fabric sleeve having an inner and outer surface. The force transmitting element includes at least one cable that runs in contact with a portion of the outer surface of the sleeve between the tensioning device and the point of contact on the bracing member. In some embodiments, the sleeve further includes a padded surface on the portion of the outer surface over which the cable is in contact. In some embodiments the sleeve is further configured with an exterior sleeve cover that covers the portion of the outer surface over which the cable is in contact. In various embodiments, the fabric sleeve includes a pocket configured to removably hold the bracing member in at least one of a medial or lateral position with respect to a joint on the limb when the sleeve is worn by the subject.

In certain embodiments, the force sensor comprises a fluid filled bladder positioned between the tensioning device and mounting. In typical embodiments the force sensor includes a pressure transducer configured to detect pressure in the bladder when force is applied by the force dosimeter and to convert the detected pressure into an electrical signal. Typically, the fluid is a gas and the force transducer is in fluid communication with the gas in the bladder through a tube. The bladder typically is made of a gas impermeable sheath and may include a compressible foam insert within the sheath. In certain embodiments, the bladder is donut shaped.

In certain embodiments, at least one, and typically each, of the force transmitting element, the dosing device, the tensioning device, the force sensor and the force indicator are releasably detachable from the mounting.

BRIEF DESCRIPTION OF THE DRAWINGS

FIG. 3A illustrates certain features of a bracing member described herein.

FIG. 3B highlights a pivotal joint of the bracing member.

FIG. 8 illustrates embodiments of a force dosimeter configured with a force sensor and force indicator. FIG. 8A is a top isometric view, FIG. 8B is a side view, FIG. 8C is a bottom isometric view and FIG. 8D highlights certain features of a processor/transducer used therein.

DETAILED DESCRIPTION OF PREFERRED EMBODIMENTS

Described herein are orthotic or prosthetic devices for applying an adjustable therapeutic amount of force to the device, to detect the amount of force applied and to provide an indication of the amount of force applied to the user. The invention includes numerous features that may be used in various configurations for a variety of devices, including, but not limited to, knee braces, elbow braces, shoulder braces, torso braces, wrist braces, finger braces, ankle braces, hip braces or any prosthetic device for which it is desirable to apply a controlled amount of force to effect a therapeutic benefit. In exemplary embodiments, the force is drawn across a natural or artificial joint of the subject. The description that follows exemplifies the features of the device in the context of a knee brace, however, one of ordinary skill in the art will be able to readily adapt the features described herein alone or in combination, to a variety of devices.

Figure 1A:
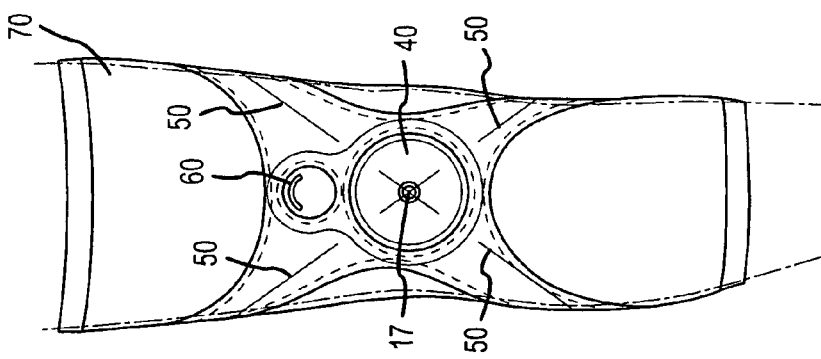
FIG. 1 illustrates left, front and right views of an exemplary embodiment of a bracing apparatus described herein having a plurality of cable force transmitting elements attached to a bracing member and a force dosimeter.
Figure 1B:
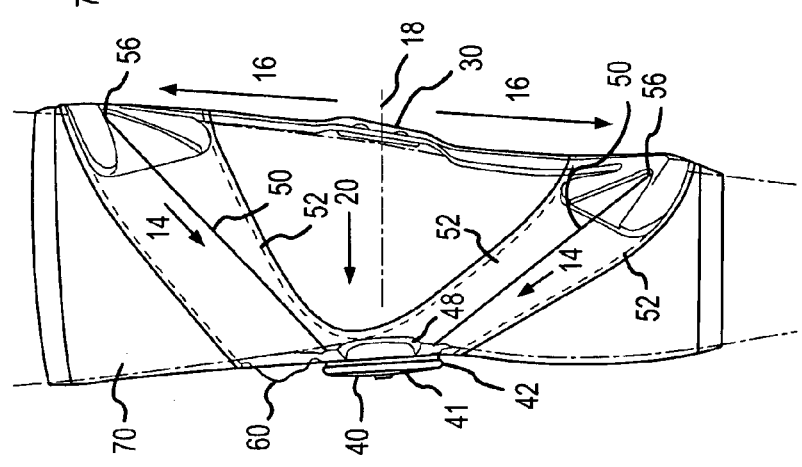
Figure 1C:
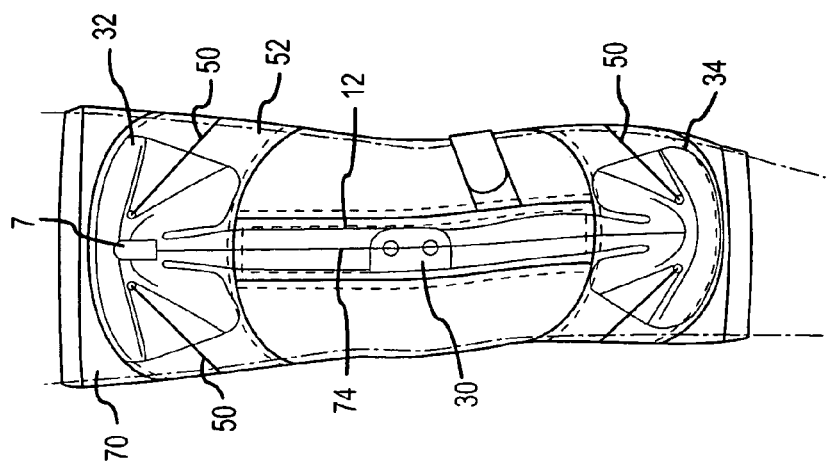

FIGS. 1A-1C depict left, front and right views of an example orthotic knee brace apparatus 10 that implements various features of the present invention. The knee brace apparatus 10 of FIG. 1 is designed to treat unicompartmental osteoarthritis, which is typically caused by degradation in either the medial or lateral compartmental spaces between the femur and the tibia in a subjects a knee. To treat unicompartmental osteoarthritis with a brace requires placing a bracing member 12 in a therapeutic position adjacent to the knee joint to draw a therapeutic amount of force across the affected compartment. The applied force is drawn along the vectors indicated by arrows 14 to urge the affected compartment between the femur and tibia apart along force vectors 16. The applied force is triangulated, meaning the force vectors 14 would meet at some vertex 17 roughly positioned at the axis of rotation 18 of the knee and adjacent to the opposite (non-affected) compartment so that a resultant force 20 is directed inwardly (or outwardly) in a plane parallel to, or more typically collinear with, the axis of rotation 18 of the knee. The bracing member 12 can be positioned on the lateral or medial side of the knee so that the resulting vector 20 can be directed in either the valgus (outward) or varus (inward) direction, depending on whether the medial or lateral compartment is affected, respectively.

As described in more detail below, the bracing member 12 includes upper 22 and lower 24 connecting arms joined to corresponding upper 32 and lower shell members 34. The shell members 32, 34 are each connected to a force dosimeter 40 engaged with a mounting 70 and connected to the shell members 32, 34 through a force transmitting element(s) 50. The force dosimeter 40 is comprised of at least two functional components—a tensioning device 42 and dosing control device 41, which may be separable or integrally formed. The dosing control device 41 is an assembly for adjusting the amount of force drawn by the tensioning device 42 on the force transmitting element(s) 50. In the knee brace apparatus 10, the force dosimeter 40 applies force to the force transmitting elements 50 to draw the force vectors 14 from the opposite side of the joint from the affected compartment where the bracing member 12 is located. The amount of force drawn in detected by a force sensor 58. The force sensor is operably connected to a force indicator 60 that provides an indication of the amount of force detected.

Figure 2:
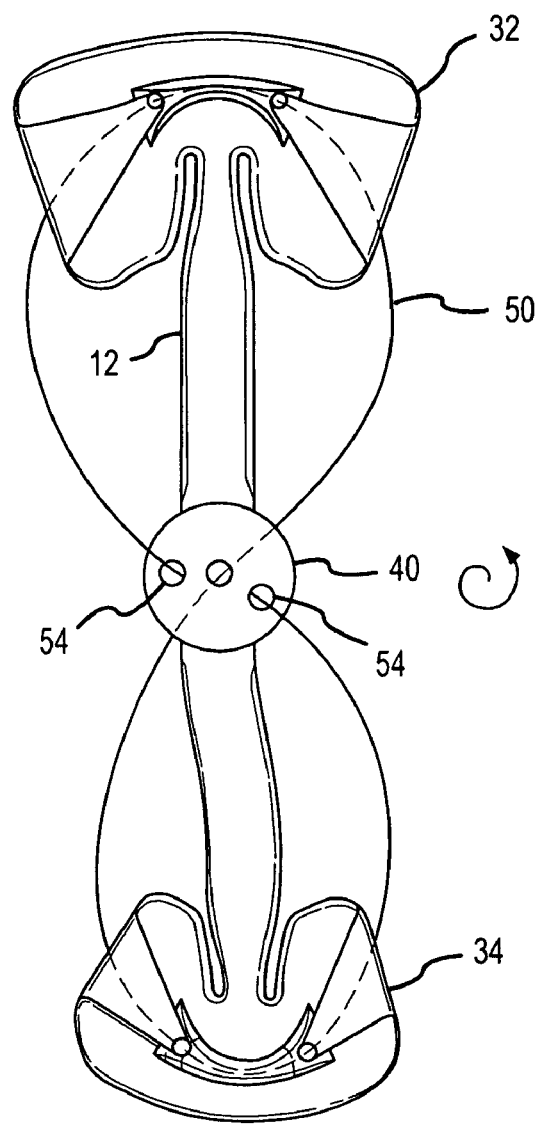
FIG. 2 illustrates a bracing member configured with a single cable as a force transmitting element.

The force transmitting element(s) 50 can be any flexible or rigid material of any suitable shape through which a force can be drawn by the force dosimeter 40. Suitable examples of the force transmitting element(s) 50 include, but are not limited to a rope, a cable, a strap, a mesh, an elastic band and the like. In the example depicted in FIG. 1, the force transmitting element(s) 50 is a cable. In certain embodiments, as depicted in FIG. 2, a single cable can be used, which has its ends 54 attached to the force dosimeter 40, and which loops around the upper and lower shell members 32, 34 of the bracing member 12. Alternatively, the ends 54 may be attached to the upper 32 or lower 34 shell members or both, and medial portion of the force transmitting element(s) 50 can be operably engaged with the force dosimeter 40.

In any case, as best depicted in FIG. 1A, the force transmitting element(s) 50 forms an "X" pattern around the limb with the vertex 17 of the X being generally parallel to, and roughly colinear with, the axis of rotation 18 of the knee on the lateral side opposite the bracing member 12. In the embodiment depicted in FIG. 1, a plurality of individual cables 50 is used to form the "X" shaped pattern, each having one end attached to the force dosimeter 40 and the other end attached to the bracing member 12 at the upper and lower shell members 32, 34. As will be described in more detail below, one end 54 of each of four cables 50 is attached to four tensioning devices 42 within the force dosimeter 40. The other end 56 is attached to the upper and lower shell members 32, 34 of the bracing member 12. In this embodiment, force is simultaneously applied to each of the cables 50 from each of the tensioning devices 42 by adjusting the force dosimeter 40 with the dosing device 41.

The function of the force dosimeter 40 and arrangement of the force transmitting elements 50 in the brace apparatus 10 of FIG. 1 is to adjustably apply a uniform force along each of four force vectors 14, two of which are located above the knee joint along dorsal and ventral surfaces of the limb, and two of which are located below the knee joint along dorsal and ventral surfaces of the limb. To apply the force along vectors 14, the dosing device 41 of the force dosimeter 40 is used to actuate the tensioning device 42 to apply increasing or decreasing force to the force transmitting element(s) 50. As force is applied by the force dosimeter 40, the force transmitting elements 50 are pulled along force vectors 14 which in turn draws the upper and lower arms 22, 24 of the bracing member 12 upward and downward along force vectors 16 to urge the affected compartment of the knee apart.

FIG. 3A depicts an embodiment of the bracing member 12 in more detail. The bracing member is typically made of a rigid or semi-rigid material, and includes the upper arm connector 22 and a lower arm connector 24, which are interconnected by a pivoting element 30 at one end and joined to the shell members 32, 34 at the other end. In a typical embodiment, the shell members 32, 34 and connector arms 22, 24 are integrally formed, for example, of molded or stamped plastic, metal or fiber material, such as carbon fiber. In other embodiments, the connector arms 22, 24 and shell members 32, 34 can be made as modular interconnecting components.

The pivoting element 30 permits the upper 22 and lower 24 arms to pivot with respect to one another parallel to the axis of rotation 18 of the subject's knee as the knee is extended or bent. FIG. 3B is a cut-away view illustrating one embodiment of the pivoting element 30. In this embodiment, the pivoting element 30 located at the proximal ends 28 of the upper and lower connecting arms 22, 24, is configured with intermeshing gears 31 and 33 that engage one another to provide a smooth rotation of the upper and lower connecting arms 22, 24 about an arc 37 that is at least 45 degrees, and more typically at least 90 degrees. The pivoting element 30 is optionally configured with a stop surface 35 that prevents pivoting of the upper and lower connecting arms 22, 24 in the opposite direction to prevent hyperextension of the knee. The use of intermeshing gears 31 and 33 is only one of many embodiments of the pivoting element 30. One of ordinary skill in the art can readily substitute other pivoting mechanisms, such as hinges, axles, hubs, bearings and the like to accomplish the function provided by the pivoting element 30.

Turning again to FIG. 3A, the distal portions 26 of the connecting arms 22, 24 (i.e., the portions extended away from the pivoting element 30) are joined to upper and lower shell members 32, 34 at a central joining region 36 thereof. The shell members 32, 34 are conformed to fit onto the lateral or medial surfaces of the limb. Many configurations of shell members can be envisioned. In the embodiments depicted herein, the shell members 32, 34 are configured with a pair of adjacent wing members 38 that extend in opposite directions away from the central joining region 36. Each wing member 38 includes a guide surface 39, which is a surface over which a force transmitting element(s) 50 will ride. The guide surface 39 depicted in FIG. 2A is configured as a depression in the shell members 32, 34. Each of the shell members 32, 34 further include at least one attachment element 57. The attachment elements 57 are configured to receive the force transmitting elements 50 that are used to draw the force vectors 14 from the brace apparatus 10.

As depicted, the attachment elements 57 are configured to detachably connect to an end 56 of the cable 50 serving as the force transmitting element(s) 50. In other embodiments, the attachment element 57 can be merely a loop or other mechanism that holds the force transmitting element(s) 50 in fixed position on the shell members 32, 34. Thus, the attachment element 57 can be configured in many ways, depending on the type of force transmitting element(s) 50 used. By way of example, but not limitation, the attachment element can be a snap, a button, a connector, a fastener, interlocking fabric loops (e.g., Velcro™) or the like.

One of the features of the bracing member 12 that is useful in many devices, is that the distal portions 26 of at least one, and typically both, of the upper 22 and lower 24 connecting arms have a smaller dimension (e.g., a smaller cross sectional area) than the proximal portion 28 of the bracing arms 22, 24 proximal to the pivoting element 30. More particularly, the thickness, width or both thickness and width, are less at the distal portion 26 than the proximal portion 28. As shown, the distal portion 26 tapers in both thickness and width from an outer aspect of the proximal portion to the end of the distal portion 26. In addition, the configuration of the shell members 32, 34 with respect to the distal portion 26 of the bracing arms 22, 24 is such that an open channel area 43 is formed between the inner edges of the wings 38 and the distal portion 26 of the connecting arms 22, 24. The smaller dimension of the distal portion 26 provides less resistance to twisting and flexing than the proximal portion 28, so that the distal portion 26 of the arm 22 attached to the shell members 32, 34 can twist somewhat about the longitudinal axis and flex somewhat in the lateral and medial directions. This provides a more sure and more comfortable fit of the brace apparatus 10 by facilitating incidental flexing and twisting of the brace 10 as the limb is moved in various directions. This flexing and twisting is further promoted by the channel 43 formed between the inner edges of the wings 38 and the distal portion 26 of the connecting arms 22, 24.

Returning now to FIG. 1, in certain embodiments, the foregoing elements of the brace apparatus 10 are detachably engaged within a mounting to complete the brace apparatus 10. As will be described in more detail hereafter, the brace apparatus 10 includes a sleeve mounting 70 for mounting the bracing member 12, force transmitting elements 50, force dosimeter 40 and force indicator 60. In certain embodiments, a padding 52 may be included on a surface of the sleeve mounting 70 as a contact surface for the force transmitting elements 50, which provides increased comfort to the wearer.

Figure 4A:
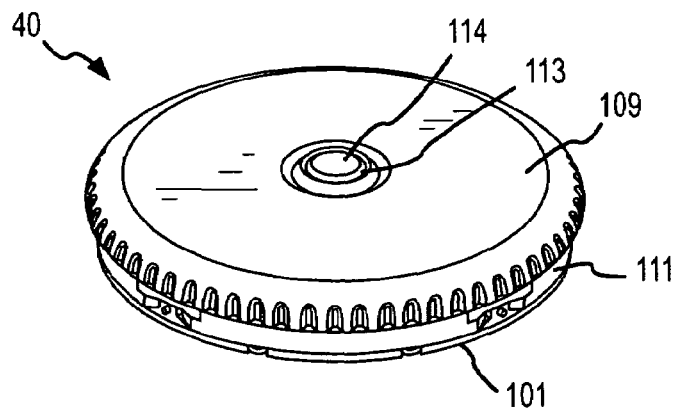
FIG. 4 shows top and side views of one embodiment of a force dosimeter described herein.
Figure 4B:
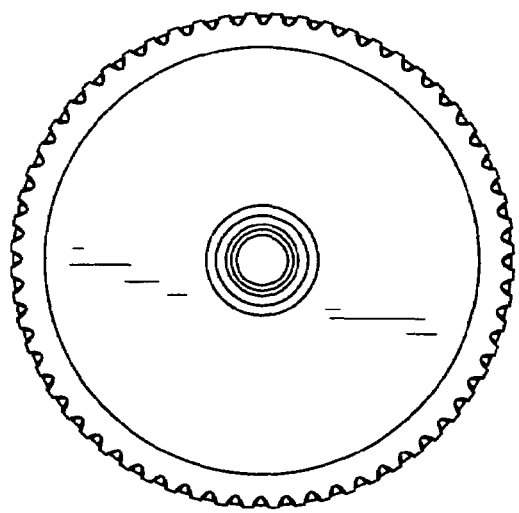
Figure 4C:
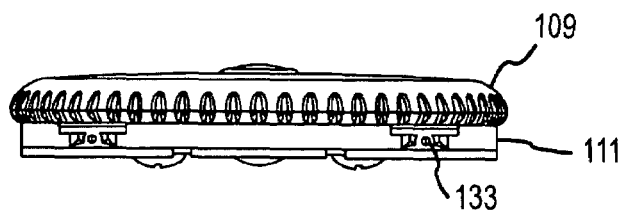
Figure 5:
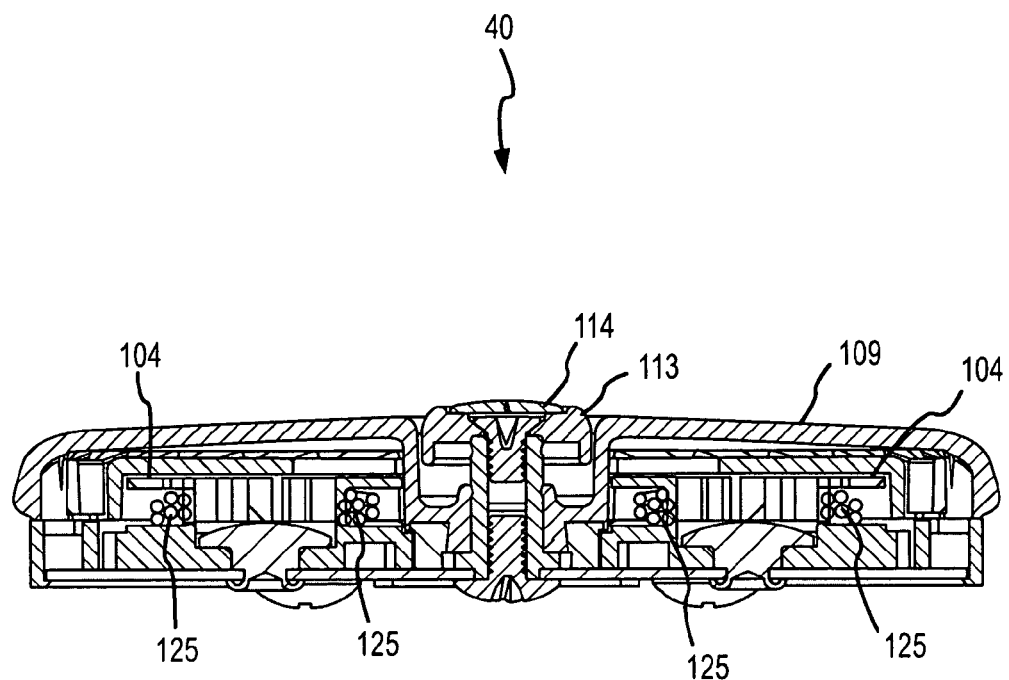
FIG. 5 is a cut-away side view of the dosimeter of FIG. 4.
Figure 6:
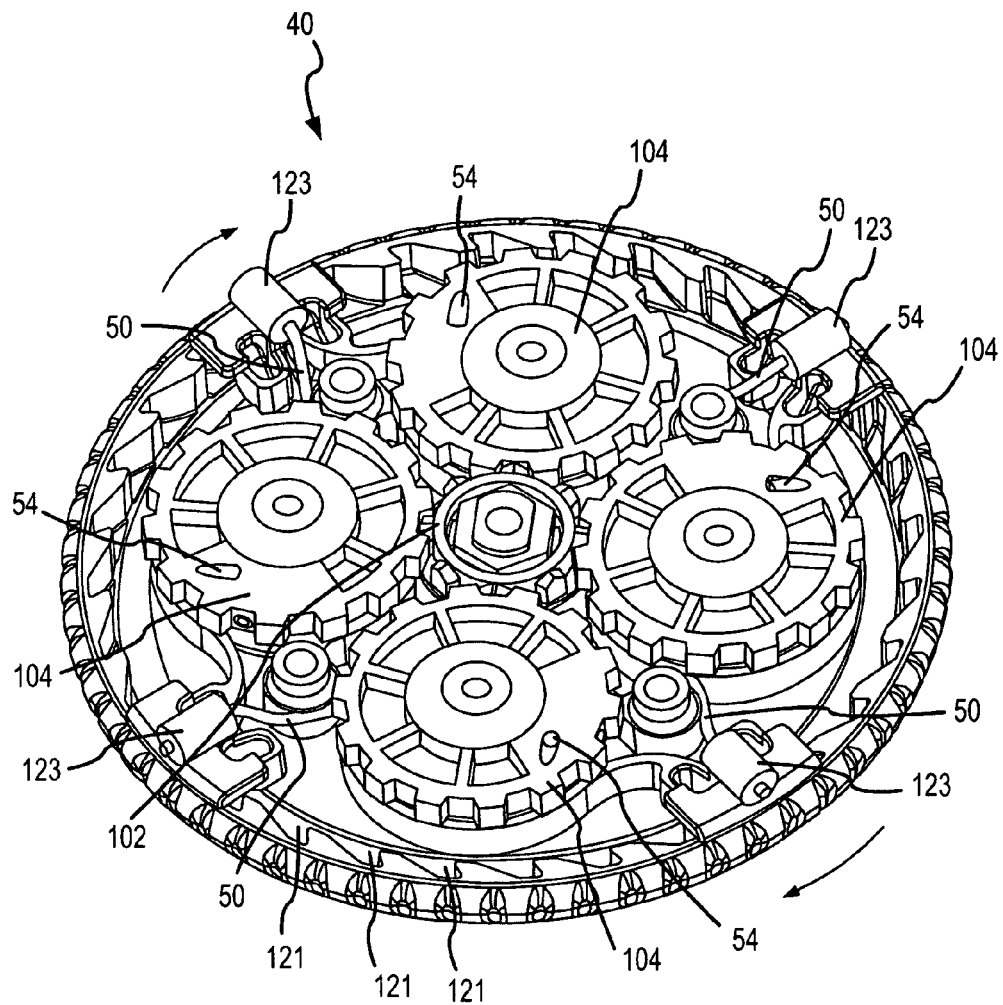
FIG. 6 is a cut-away top isometric view of the dosimeter of FIG. 4.

Turning now to the force dosimeter 40, FIG. 4A shows an isometric view, FIG. 4B shows a top view, and FIG. 4C shows a side view of one exemplary embodiment of the force dosimeter 40. FIG. 5 shows a cross-sectional view of this embodiment along line A-A, while FIG. 6 shows a cutaway isometric view of the same. This embodiment includes a top cover 109, an inner cover 111 and a base plate 101. The inner cover 111 includes entry ports 123 by which, one end 54 of the force transmitting element(s) 50 can be introduced to operably engage the tensioning device 42 component of the force dosimeter 40.

The top cover 109 forms part of the dosing device 41, which in this embodiment includes a ratcheting assembly. More particularly, the underside of the top cover 109 includes a flexible pawl 119 shown in FIG. 7 that is positioned to engage splines 121 located at the inner circumferential edge of the top cover 109 as shown in FIG. 6. A jewel button assembly comprising a jewel base 113 and jewel sticker closing mechanism 114 are configured in the top cover 109. When the jewel sticker closing mechanism 114 is in a first (locking) position, the pawl 119 on the underside of the top cover 109 engages one of the splines 121 so that the top cover 109 is in a locked position with respect to rotation in one direction about the axis of the jewel sticker.

Because the pawl 119 is flexible, the top cover 109 (and anything attached thereto) can be rotated in a forward direction indicated by the arrow in FIG. 6, causing the pawl 119 to flex and slip out of one slip spine 121 and incrementally engage the next adjacent slip spline 121 as the top cover 109 is rotated in the forward direction. In this first "locking" position, the top cover 109 cannot be rotated in the opposite direction because of the engagement of the pawl 119 in the slip spine 121 prevents the pawl 119 and attached top cover 109 from moving backwards. Pulling upward on the top cover 109 while depressing the jewel sticker 114 to release it from the jewel base 113 permits the top cover 109 to be raised to a second, "unlocked" position, where the pawl 119 is disengaged from the splines 121, allowing the top cover 109 to be freely rotated in a backward direction counter to the direction of the arrow.

The top cover 109 is operably linked to a spur gear 102, which in turn engages spring gears 104. The spring gears 104 are attached to one end 54 of force transmitting cable 50. The gear portion of the spring gears 104 forms part of the tensioning device 42 because turning the top cover 109 in the tightening direction causes the spring gears 104 to wind the force transmitting element(s) 50 around a spindle to thereby apply force on the force transmitting elements. The spring gears 104 are also engaged with a torsion spring 125 that provides a retracting force to prevent the force transmitting element(s) 50 from going limp when the top cover 109 is in the unlocked position disengaged from the splines 121. When the top cover 109 is in the locking position and is advanced in the forward direction indicated by the arrow, the spur gear 102 drives the spring gears 104 to tighten the force transmitting cables 50 attached thereto. When the top cover is 109 is raised to the unlocked position and turned in the opposite direction, the spring gears 104 are driven the opposite direction to thereby reduce the applied force.

In an alternative configuration (not shown) instead of winding the force transmitting cables 50 around the spring gear 104 to impart force, the spring gears 104 can be configured so that the torsion spring 125 applies the force directly. In this embodiment, when the spring gears are turned in the tightening direction, the torsion springs 125 are also tightened. The torsion springs would be attached to the ends 54 of the force transmitting cables 50 so that the tension in the torsion springs 125 is thereby imparted to the force transmitting cables 50. In this embodiment, the force transmitting cables 50 would have some degree of elasticity in the applied force and the amount of elasticity would correspond to the resilience of the torsion spring 125. The elasticity would being less when the torsion spring 125 is tightly wound and greater when loosened.

Figure 7:
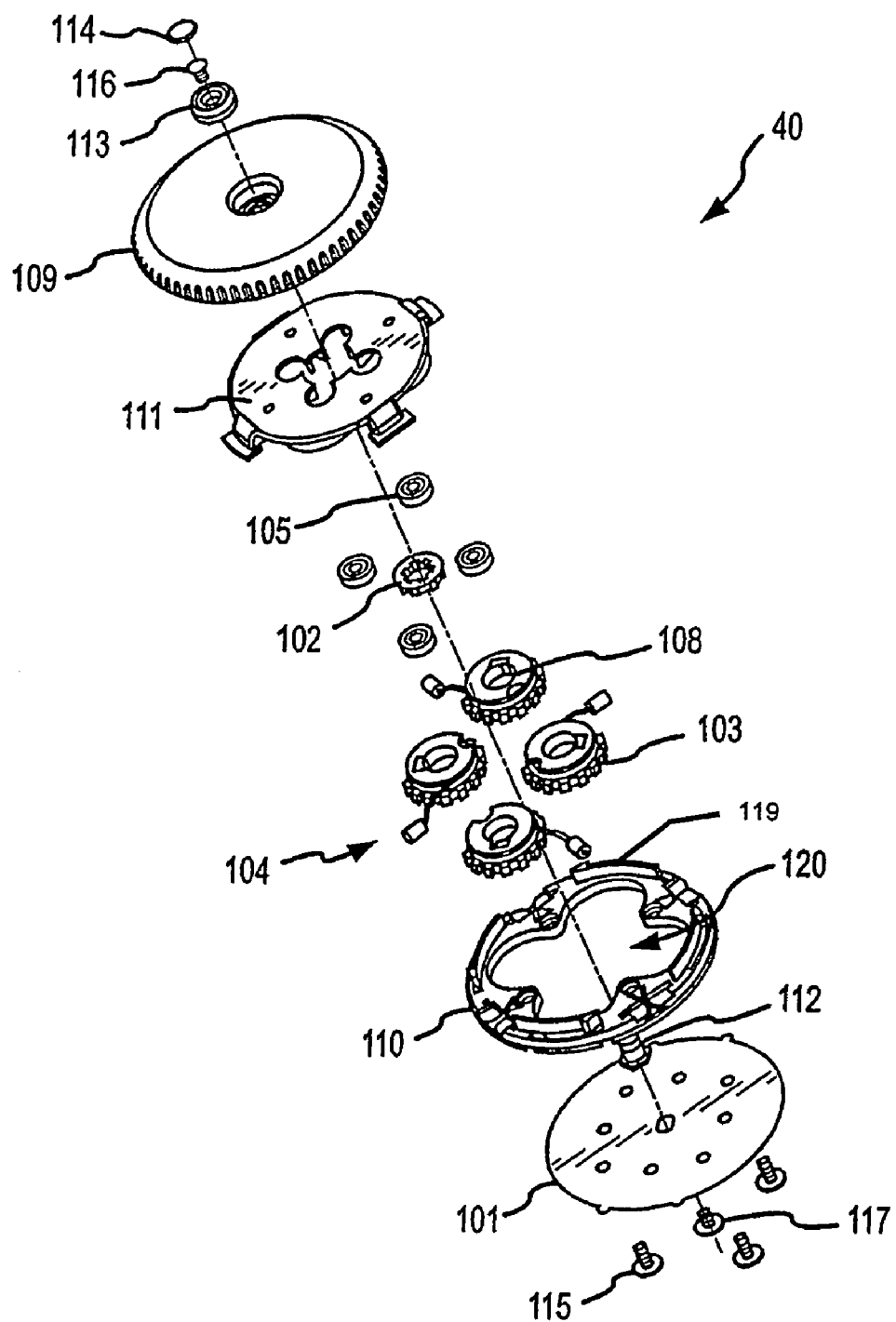
FIG. 7 is an exploded view of the dosimeter of FIG. 4.

FIG. 7 is an exploded view of the force dosimeter 40 assembly shown in FIGS. 4-6. The force dosimeter 40 assembly includes the base plate 101 positioned beneath a base frame 110. The base frame 110 has a cruciform aperture 120 disposed in the middle thereof. Each of the four quarter portions of the of the cruciform aperture 120 are dimensioned to house a separate spring gear assembly 104. Each spring gear 104 includes the torsion spring 125 configured to engage the interior of a toothed gear spindle 103 so that the torsion spring 125 provides a spring force against turning of the toothed gear spindle 103 in one direction of rotation. Each toothed spindle 103 is configured with a cable connector 108 configured for releasably connecting to the end 54 of a force transmitting cable 50. The four spindles 103 are simultaneously driven by the central spur gear 102 that has teeth configured to engage the teeth of the spindles 103. When engaged, as the spur gear 102 is turned in a tightening direction, each of the spindles are simultaneously rotated in counter resistance to the torsional force of the torsion springs 105. The more the spindles 103 are rotated by the gear 102, the more counter resistance is transmitted from the spindles 103 to the cables 50 attached to the cable connector 108. The reverse occurs when the spur gear 102 is turned in the opposite direction, whereby less force is transmitted from the spindles 103 to the cables 50.

The inner cover 111 is fitted over the base frame 110 and base 101. The inner cover 111 contains a set of eyelets which form the entry port 123 into which the cable ends 54 are threaded for attachment to the cable connector, and thereby to the spring gears 104. The top cover 109, containing the pawl and splines 121 is fit over the inner cover, that includes a central axle (not shown) that engages the spur gear 102 with pin bearing 112. The jewel sticker 114 and jewel sticker base 113 for moving the top cover 109 into the lock and unlocked positions are positioned in the central portion of the top cover 109. The jewel sticker assembly 113, 114 is held in place by fastener 116, and the entire dosimeter 40 is held together by machine screws 115 and 117.

Turning now to FIG. 8, the amount of force applied by the dosimeter 40 is detected by a force sensor 56 also removably mounted on the sleeve mounting 70. In the exemplary embodiment depicted in FIG. 8, the force sensor 56 is a multicomponent assembly that includes a resiliently deformable element 58, a force transducer 59 and a force indicator 60. The resiliently deformable element 58 can be a spring, an elastic band, a fluid containing bladder and the like, or various combinations of the same. In the embodiment depicted in FIG. 8, the resiliently deformable element 58 is a donut shaped bladder 58 that contains a volume of air, and optionally contains a donut shaped resilient sponge 57. The resilient sponge 57 serves to maintain the shape of and thereby provide a deformable rigidity to the bladder 58 so that positive air pressure is not required to inflate the bladder and less air volume is needed to exert pressure in the bladder 58.

The bladder 58 is located on the brace apparatus 10 between the force dosimeter 40 and the mounting 70. This places the bladder 58 between the force dosimeter 40 and the subjects joint when the brace apparatus is donned as depicted in FIG. 1B. Returning to FIG. 8, the bladder 58 is held in position between retainer plates 63 and 65. As incremental force is applied from the tensioning device 42 by actuating the force dosimeter 40, the air fluid in the bladder 58 is compressed thereby increasing pressure in the bladder. A tube 61 transmits the air pressure in the bladder to a force (e.g., pressure) transducer 59, which is located within the force sensor 56. The pressure is transduced into an electronic signal indicative of the amount of force and the electronic signal is in-turn translated into a visible, audible or other empirically detectable signal that is indicated by the force indicator 60.

Turning to FIG. 8D in certain embodiments, the transducer 59 can be a multicomponent electronic assembly that includes various components. The transducer may include a processor 59a operably connected to a primary force transducer 59b. The primary force transducer 59b initially converts the detected force into an electronic signal. The processor 59a transforms the electronic signal into an information signal indicative of the amount of force applied and also controls the display of the force indicator 60 so that gives a signal indicative of the amount of force applied. The processor 59a may also convert the electronic signal into data indicative of the amount of force applied. That data may be stored in a memory 59c configured with processor 59a. In certain embodiments, the data stored in the memory 59c may be downloaded through a data port 59e to an external handheld or stand alone computer or display, or to an external force indicator. In other embodiments, the data may also be sent to a wireless data transmission device 59d configured with the processor 59a to wirelessly transmit the data to an external or remotely located computer device or display screen. In typical embodiments, the wireless data transmission device 59d uses a conventional data transmission protocol such as BlueTooth, or other protocol. With this configuration, a health service professional can monitor the force being applied by the brace apparatus on the subject through the course of a day and may make adjustments in the recommended positioning or amount of force needed based on real time data having been recorded and transmitted to the professional.

As depicted in the embodiment of FIG. 8, the force indicator 60 is a series of LEDs, which are incrementally lit as increasing force (e.g., pressure) is detected, thereby providing a bar type indication of the amount of force applied. Of course, any of a variety of types of force indicators can be used, including for example, a display screen, different audible signals, a gauge, a mechanical pointer and the like. Because the force indicator 60 reproducibly indicates the amount of force detected by the force sensor 56, the wearer of the brace apparatus 10 has a feedback that allows the wearer to reproducibly apply the same therapeutic amount of force each time the brace apparatus is donned.

Although the embodiments exemplified herein each illustrate the force sensor 56, force dosimeter 40, and force indicator 60 as located adjacent one another on the same side of the brace apparatus 10 adjacent the knee joint, it should be understood that these elements can be located anywhere on the brace apparatus 10 where their function can be preserved. The amount of force drawn on the force transmitting elements 50 by the dosimeter 40 is ideally, uniformly distributed to each force transmitting element(s) 50, therefore the force sensor sensing element 58 can be located across or beneath any of the force transmitting elements 50. For example, the force sensing element may be a spring assembly interposed between two ends of a force transmitting elements 50. Likewise, the force indicator 60 need not be associated with the force sensor 56 in the same housing but may separately located in a more convenient position for viewing.

Figure 9A:
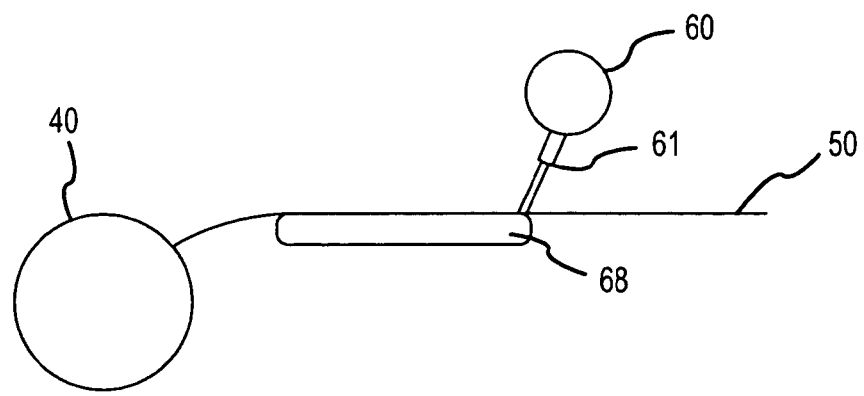
FIG. 9 depicts a few examples of alternative types force sensors and force dosimeters.
Figure 9B:
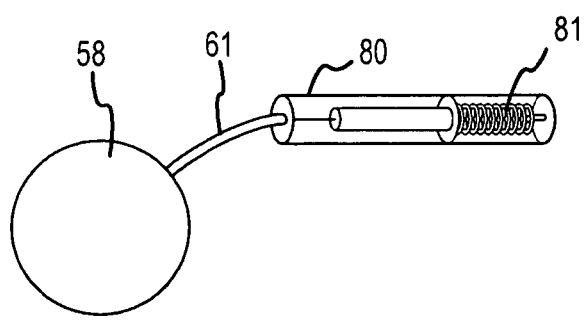

The force dosimeter 40, force sensor 56 and force indicator 60 depicted in FIGS. 1-8 herein are only illustrative of the types of devices that can be used to perform the same functions in various other embodiments. For example, as an alternative to a donut shaped resiliently deformable bladder 58 positioned between the force dosimeter and the subjects joint, a linear bladder 68 can be positioned underneath one or more of the force transmitting elements 50 as depicted in FIG. 9A. As force is drawn by the force dosimeter 40 pressure in the linear bladder 68 is detected and indicated by the force dosimeter.

In a different aspect, as an alternative to using a force transducer 59, which transduces the detected pressure into an electronic signal, a mechanical force indicator 80 could be used. In one example of a mechanical force indicator 80, a spring plunger assembly 81 is positioned in a tube and is displaced therein by a distance proportionate to the pressure in the bladder 58. A pointer could indicate the amount of pressure applied.

Figure 9C:
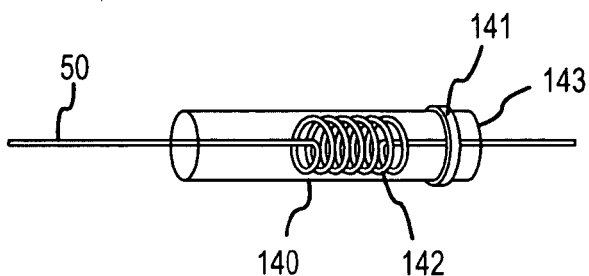

In still a different aspect, instead of using a torsion spring assembly 104 as the tensioning component of the force dosimeter 40, the force dosimeter 140 could be comprised of a compression spring 142 connected to the force transmitting element(s) 50 as depicted in FIG. 9C. Adjustment in force could be applied by turning a dosing knob 141 that engages threads 143 to adjustably depress the compression spring 142. In this and other embodiments, the functions of the force dosimeter 40 and the force indicator 60 can be combined because the relative position of the dosing knob 141 is indicative of the amount of compression, and hence the amount of force applied by the compression spring 142.

In yet another aspect, instead of using a resiliently deformable element such as a bladder 58 or spring as the force sensor 56, an electronic force sensor such as thin film resistor or piezoelectric detector can be employed to detect force. Other embodiments of force sensors 56 include, but are not limited to, strain gauges, laser based displacement sensors, capacitance displacement sensors, variable differential transformers and the like. In short, any device that can be configured by one of ordinary skill in the art to detect the force applied or drawn on the force transmitting elements 50 from the force dosimeter 40 is suitable in various embodiments.

Turning now to the mounting 70, in typical embodiments, each of the foregoing components of the brace apparatus 10 are engaged with the mounting 70 configured to fit the brace apparatus 10 on the subject. Suitable mountings include strapping, rigid materials such as plastic or metals conformed to fit the subjects limb, a fabric sleeve and the like, as well as combinations of the same. In the embodiments exemplified herein, the mounting 70 is a fabric sleeve. Another feature of the brace apparatus 10 provided herein is that the component parts may be replaceably detached from the fabric sleeve 70 so that the sleeve 70 can be washed or replaced keeping the same component parts for subsequent use.

Figure 10:
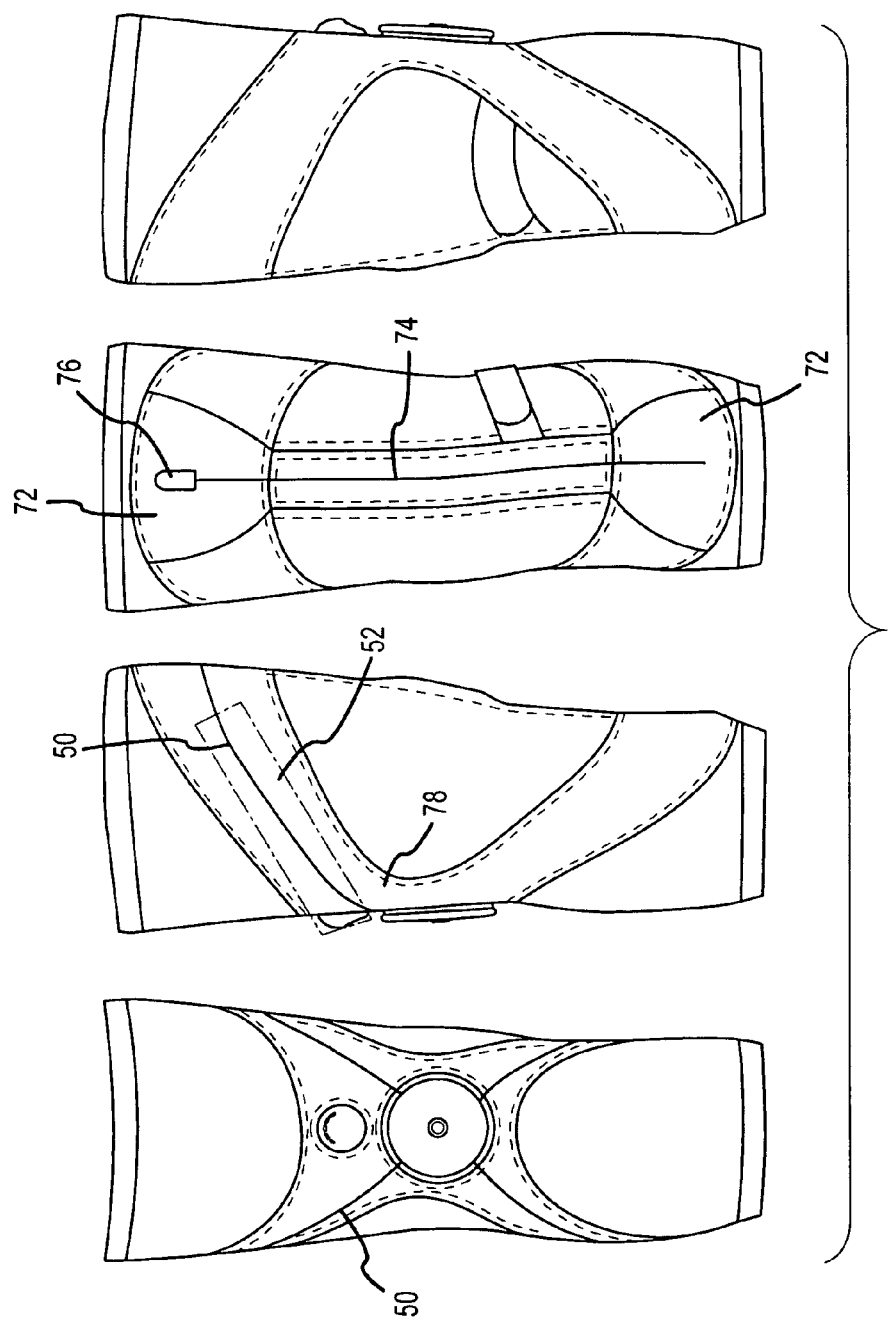
FIG. 10 depicts an example fabric sleeve mounting of a bracing apparatus disclosed herein.
Figure 11:
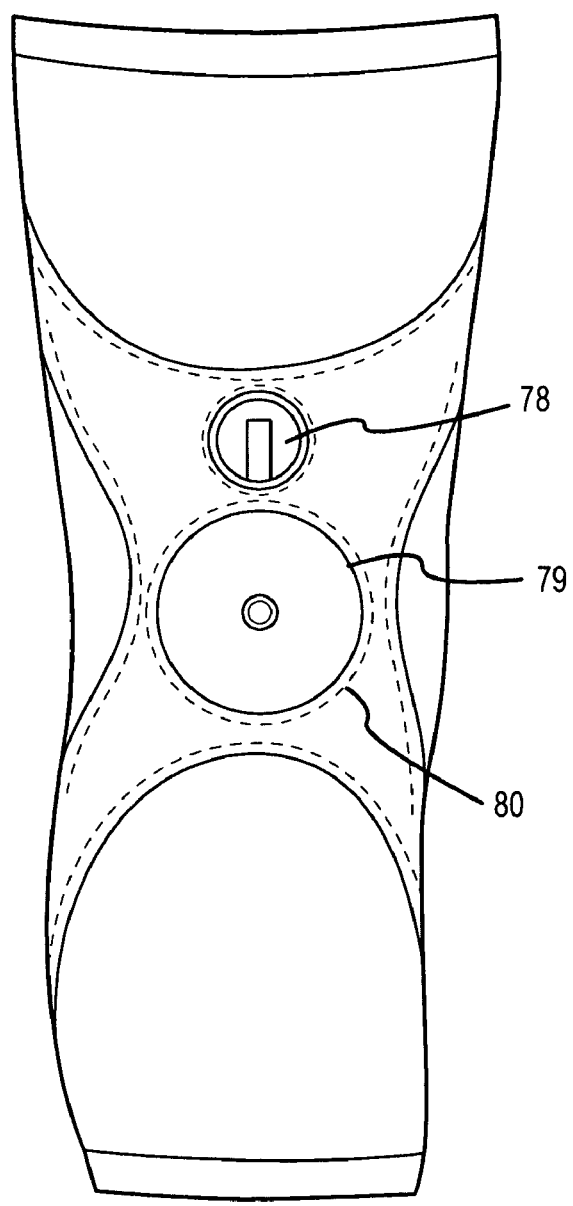
FIG. 11 depicts examples of replaceably removable connections between the sleeve mounting the force dosimeter, and force indicator.

FIGS. 1, 10 and 11 illustrate various features of certain embodiments of the sleeve mounting 70. As shown in FIGS. 1 and 10, these embodiments include a pocket 72 configured to replaceably hold the bracing member 12 in a therapeutic position when the brace apparatus 10 is worn by a subject. The interior of the pocket 72 is accessed through suitable closure mechanism, exemplified by a zipper 74. A zipper garage flap 76 can be provided to contain the handle end of the zipper 74 out of the way when the zipper 74 is used to close the pocket 72. Alternatively, or in addition, the pocket 72 may also be made accessible by covering flaps that include interlocking fabric loops and hooks to close the pocket 72. The sleeve 70 contains an interior surface (not shown) that contacts the subject's limb, and an exterior surface configured to hold the component parts in a therapeutic position on the limb. The exterior surface of the sleeve mounting 70 includes the padding 52 over which the force transmitting elements 50 are disposed. The padding 52 can conveniently be covered by a fabric cover 78 thereby forming a channel between the padding 52 and the fabric cover 78 in which the force transmitting elements 50 are disposed.

Turning to FIG. 12, in various embodiments, the force dosimeter 40, the force sensor 56 and the force indicator 60 are each replaceably detachable from the sleeve 70 by way of corresponding connectors 78 and 79. The connectors 78, 79 can be conveniently sewn into a compartment formed in the fabric sleeve 70 with appropriate stitching 80. Alternatively, the connecters 78, 79 can be bonded to the sleeve 70 or integrally molded within a rigid material included within the sleeve as a separate or integral component thereof. The connectors 78, 79 can be any type of connector having suitable strength and rigidity to hold the component parts in place and having a suitable mechanism for securely connecting the corresponding components to the sleeve 70. Example connectors include but are not limited to interlocking fabric loops a slot and tab connector, a spring loaded connector, a fastener assembly, intermeshing threads and the like.

From the foregoing it will be appreciated that, although specific embodiments of the invention have been described herein for purposes of illustration in the context of a knee brace, numerous features describe herein are useful in a variety of orthotic or prosthetic apparatus. Moreover, although exemplary embodiments of various elements of the invention have been described in detail, various modifications, substitutions or additions to these elements to provide devices that perform the same functions can be may be made without deviating from the spirit and scope of the invention. Accordingly, the invention is not limited except as by the following claims.

What is claimed is:

1. An orthotic or prosthetic apparatus, comprising:
   a bracing member secured to a mounting, the mounting operable to position the bracing member in a therapeutic position in relation to a joint on a limb of a subject;
   a plurality of force transmitting elements secured to the bracing member; and
   a device having a tensioning component and a force dosing component, the force dosing component including a ratchet assembly operable to engage the tensioning component to incrementally increase the amount of force applied to the force transmitting elements, the tensioning component including a plurality of spring gears, each spring gear releasably coupled to a respective one of the plurality of force transmitting elements and operable to apply a force to the respective force transmitting elements, each spring gear including a spindle operable to wind the coupled force transmitting element around, each force transmitting element being individually adjustable to change the force being applied to the respective transmitting element without adjusting the force being applied to the other of the plurality of force transmitting elements.

2. The orthotic or prosthetic apparatus of claim 1 wherein the ratchet assembly comprises a pawl and a plurality of splines.

3. The orthotic or prosthetic apparatus of claim 1 wherein the plurality of force transmitting elements comprise a plurality of cables.

4. The orthotic or prosthetic apparatus of claim 3 wherein the tension applied by the tensioning device is simultaneously applied to the plurality of cables when the tension is adjusted with the dosing device.

5. The orthotic or prosthetic apparatus of claim 1 wherein the ratchet assembly comprises a pawl and a plurality of splines, the pawl positioned to incrementally engage each spline when the ratchet assembly is rotated, each engagement increasing the amount of force applied to the plurality of force transmitting elements.

6. The orthotic or prosthetic apparatus of claim 5 wherein the spring gear further comprises a spring configured to maintain at least some tension in the respective force transmitting element when the ratchet assembly is disengaged from the tensioning component.

7. The orthotic or prosthetic apparatus of claim 6 wherein the spring comprises a torsion spring operable to maintain tension on the force transmitting elements when the pawl is disengaged from the splines.

8. An orthotic or prosthetic apparatus comprising:
   a bracing member secured to a mounting, the mounting configured to position the bracing member in a therapeutic position in relation to a joint on a limb of a subject;
   a first and second force transmitting elements secured to the bracing member; and
   a ratchet assembly having a first spring gear having a first spindle and a second spring gear having a second spindle, an end of the first force transmitting element coupled to the first spring gear, the first force transmitting element configured to wind around the first spindle and place the first force transmitting element in tension when the ratchet assembly is rotated, an end of the second force transmitting element coupled to the second spring gear, the second force transmitting element configured to wind around the second spindle and place the second force transmitting element in tension when the ratchet assembly is rotated, the tension in the first and the second force transmitting elements being individually adjustable relative to the other of the first and second force transmitting element.

9. The orthotic or prosthetic apparatus of claim 8 wherein an end of the first and second force transmitting elements are releasably secured to the bracing member.

10. The orthotic or prosthetic apparatus of claim 8 further comprising a third and fourth force transmitting element and the ratchet assembly further comprising a third spring gear having a third spindle and a fourth spring gear having a fourth spindle, an end of the third force transmitting element releasably coupled to the third spring gear, the third force transmitting element configured to wind around the third spindle and place the third force transmitting element in tension when the ratchet assembly is rotated, an end of the fourth force transmitting element releasably coupled to the fourth spring gear, the fourth force transmitting element configured to wind around the fourth spindle and place the fourth force transmitting element in tension when the ratchet assembly is rotated, the tension in the first, second, third and fourth force transmitting elements being individually adjustable relative to the other of the first, second, third, and fourth force transmitting element.

11. The orthotic or prosthetic apparatus of claim 8 wherein the ratchet assembly comprises a pawl and a plurality of splines, the pawl arranged to incrementally engage each of the plurality of splines to increase the amount of force being applied to the first and second force transmitting elements as the ratchet assembly is rotated.

12. The orthotic or prosthetic apparatus of claim 11 wherein the first and second spring gears each comprise a spring configured to maintain at least some tension to its respectively coupled first and second force transmitting element when the pawl is disengaged from any one of the plurality of splines.

13. An orthotic or prosthetic apparatus, comprising:
a bracing member attached to a mounting;
a plurality of force transmitting elements attached to the bracing member; and
a ratchet assembly having a plurality of spring gears, each spring gear coupled to a respective force transmitting element, each spring gear operable to apply tension to the respectively coupled force transmitting element when the ratchet assembly is rotated, each spring gear configured to be individually adjustable to change the tension in the respectively coupled force transmitting element without changing the tension in the other of the plurality of force transmitting elements.

14. The orthotic or prosthetic apparatus of claim 13 wherein the plurality of force transmitting elements comprise a plurality of cables.

15. The orthotic or prosthetic apparatus of claim 13 the ratchet assembly further comprising a top cover coupled to a spur gear, the spur gear coupled to each of the spring gears, the ratchet assembly further configured to engage the spring gears when the top cover is rotated.

16. The orthotic or prosthetic apparatus of claim 13 wherein the ratchet assembly comprises a pawl and a plurality of splines, the pawl positioned to incrementally engage each of the plurality of splines to increase the amount of force being applied to the plurality of force transmitting elements as the ratchet assembly is rotated.

17. The orthotic or prosthetic apparatus of claim 13 wherein each of the plurality of force transmitting elements are coupled to a spring configured to maintain at least some tension on the respectively coupled force transmitting element when the ratchet assembly is disengaged.

18. The orthotic or prosthetic apparatus of claim 13 wherein the plurality of force transmitting elements are removeably secured to the bracing member.

* * * * *